United States Patent [19]

Ulrich et al.

[11] Patent Number: 5,728,735
[45] Date of Patent: Mar. 17, 1998

[54] PHARMACEUTICAL COMPOSITION CONTAINING R-α-LIPOIC ACID OR S-α-LIPOIC ACID AS ACTIVE INGREDIENT

[75] Inventors: Heinz Ulrich, Niedernberg; Carl-Heinrich Weischer, Bonn; Jürgen Engel, Alzenau; Helmut Hettche, Dietzenbach, all of Germany

[73] Assignee: Asta Pharma Aktiengesellschaft, Frankfurt, Germany

[21] Appl. No.: 794,310

[22] Filed: Feb. 3, 1997

Related U.S. Application Data

[62] Division of Ser. No. 935,656, Aug. 26, 1992, abandoned, which is a continuation of Ser. No. 610,215, Nov. 8, 1990, abandoned.

[30] Foreign Application Priority Data

Nov. 9, 1989 [DE] Germany .......................... 39 37 323.1

[51] Int. Cl.⁶ .................................................. A61K 31/20
[52] U.S. Cl. .................................................. 514/560
[58] Field of Search .......................................... 514/560

[56] References Cited

U.S. PATENT DOCUMENTS

| | | | |
|---|---|---|---|
| 3,577,551 | 5/1971 | Murakami et al. | |
| 4,705,867 | 11/1987 | Giray et al. | 549/39 |
| 4,800,044 | 1/1989 | Giray et al. | 560/152 |
| 4,966,732 | 10/1990 | Giray et al. | 560/152 |

FOREIGN PATENT DOCUMENTS

| | | |
|---|---|---|
| 0159519 | 10/1985 | European Pat. Off. . |
| 6439 | 11/1968 | France . |
| 6518M | 1/1969 | France . |
| 1668887 | 7/1971 | Germany . |
| 60-184011 | 9/1985 | Japan . |
| 620266 | 7/1978 | U.S.S.R. . |

OTHER PUBLICATIONS

Egan et al., "Radical Scavenging as the Mechanism for Stimulation of Prostaglandin Cyclooxygenase and Depression of Inflammation by Lipoic Acid and Sodium Iodide", Prostaglandins, Dec. 1978, vol. 16, No. 6, pp. 861–869.

Szabo, "Experimental Basis for a Role for Sulfhydryls and Dopamine in Ulcerogenesis: A Primer for Cytoprotection–Organoprotection," Klin Wochernchr (1986) 64 (Suppl VII): 116–122.

Gracyk et al., "Influence of Anti–Inflammatory Agents on the Nonspecific Component of Human Neutrophil Chemotatic Deactivation," Federation Proceedings, Mar. 1, 1980, vol. 39, No. 3, Part I.

Cesobari et al., "Drogas citoprotectoras de la mucosa gastrica, ante la agresion del etanol," Trabajos Originales, Rev. Exp. Enf. Ap. Digest, 7, 3 (329–232), 1988.

*Primary Examiner*—Zohreh Fay
*Attorney, Agent, or Firm*—Cushman Darby & Cushman IP Group of Pillsbury Madison & Sutro LLP

[57] ABSTRACT

Pharmaceutical compositions and processes for their preparation containing R-α-lipoic acid or S-α-lipoic acid or pharmaceutically acceptable salts thereof. The pharmaceutical compositions have a cytoprotective activity and are suitable for combatting pain and inflammation.

10 Claims, No Drawings

PHARMACEUTICAL COMPOSITION CONTAINING R-α-LIPOIC ACID OR S-α-LIPOIC ACID AS ACTIVE INGREDIENT

This is a division of application Ser. No. 07/935,656, filed on Aug. 26, 1992, now abandoned, which was a continuation of 07/610,215 filed Nov. 8, 1990, which is now abandoned.

The present invention relates to pharmaceutical compositions containing R-α-lipoic acid or S-α-lipoic acid as an active ingredient. The compositions are useful because they inhibit, for example, acute inflammation as well as inflammatory pain and they possess a specific cytoprotective activity.

BACKGROUND OF THE INVENTION

α-lipoic acid is 1,2-dithiacyclopentane-3-valeric acid. α-lipoic acid is widely distributed in plants and animals in the form of the R-enantiomer; it acts as coenzyme in many enzymatic reactions, constitutes a growth factor for a number of bacteria and protozoa and is used in death-head fungus poisoning. In addition, the α-lipoic acid racemate displays anti-inflammatory, antinociceptive (analgesic) and cytoprotective properties.

SUMMARY OF THE INVENTION

It has now surprisingly been found that, in the case of the purely optical isomers of α-lipoic acid (R- and S-form, i.e. R-α-lipoic acid and S-α-lipoic acid), unlike the racemate, the R-enantiomer mainly has an anti-inflammatory activity and the S-enantiomer mainly has an antinociceptive activity, the anti-inflammatory activity of the R-enantiomer also, for example, being stronger by a factor of 10 than that of the racemate. The antinociceptive (analgesic) activity of the S-enantiomer is for example stronger by a factor of 5 to 6 than that of the racemate. The enantiomers therefore constitute very much more specific and stronger acting active substances than the racemate.

The following differences exist in particular in comparison to α-lipoic acid, i.e. to the racemate:

The R-enantiomer acts mainly as an anti-inflammatory and the S-enantiomer mainly as an analgesic, the optical isomers of α-lipoic acid being a number of times stronger (for example by at least a factor of 5) than the racemate of -lipoic acid.

It is therefore an object of the present invention to provide improved pharmaceutical compositions which have, in particular, analgesic and anti-inflammatory activity.

The invention relates to pharmaceutical compositions containing as active ingredient either R-α-lipoic acid or S-α-lipoic acid (i.e. the optical isomers of α-lipoic acid) or a pharmaceutically acceptable salt of these optical isomers of α-lipoic acid, the preparation thereof and the use of the optical isomers of α-lipoic acid or salts thereof for the preparation of appropriate pharmaceutical compositions. These are particularly suitable for combatting pain and inflammation. A cytoprotective activity is also obtained.

The amounts by weight set out herein relate, in each case, to the purely optical isomers of α-lipoic acid, i.e. not to the salts. When salts are used, the appropriate amounts must correspond in each case to the amounts of the free acid and be increased according to the gram-molecular weight of the salt.

The optical isomers of α-lipoic acid, i.e. R-α-lipoic acid and S-α-lipoic acid are preferably used as free acids. In aqueous solutions the salts are preferably used with pharmaceutically acceptable salt formers.

The preparation of R-α-lipoic acid and S-α-lipoic acid and of salts thereof is effected in known manner or in an analogous manner.

Salt formers that may be considered for R-α-lipoic acid and S-α-lipoic acid are, for example, conventional bases or cations which are physiologically acceptable in the salt form. Examples include: alkali metals or alkaline earth metals, ammonium hydroxide, basic amino acids such as arginine and lysine, amines having the formula $NR_1R_2R_3$ in which the radicals $R_1$, $R_2$ and $R_3$ are the same or different and represent hydrogen, $C_1$–$C_4$-alkyl or $C_1$–$C_4$-oxyalkyl, such as mono- and diethanolamine, 1-amino-2-propanol, 3-amino-1propanol; alkylene diamine with an alkylene chain consisting of 2 to 6 carbon atoms, such as ethylenediamine or hexamethylene tetramine, saturated cyclic amino compounds having 4–6 ring carbon atoms such as piperidine, piperazine, pyrrolidine, morpholine; N-methylglucamine, creatine, tromethamine.

In, for example, the acid writhing pain test in the mouse and in the Randall-Selitto inflammatory pain test in the rat, the S-enantiomer (S-α-lipoic acid) displays an analgesic activity (peroral application) which is superior by at least a factor of 5 or 6 to that of α-lipoic acid (i.e. the racemate).

Thus, for example, the above mentioned acid writhing test yielded an analgesically active $ED_{50}$ of the S-α-lipoic acid of 10.2 mg/kg per os ($ED_{50}$ of the racemate 51.3 mg/kg per os). In the above mentioned Randall-Selitto test, the analgesically effective $ED_{50}$ of S-α-lipoic acid is 7.5 mg/kg per os ($ED_{50}$ of the racemate 45.9 mg/kg).

In, for example, carragheen-induced oedema in the rat the R-enantiomer (R-α-lipoic acid) shows an anti-inflammatory activity (peroral application) which is superior by at least a factor of 10 to that of racemic α-lipoic acid.

For example, the above mentioned carragheen-induced oedema test yielded an anti-inflammatorily active $ED_{50}$ of the R-enantiomer of 4.9 mg/kg per os ($ED_{50}$ of the racemate 49.7 mg/kg).

The minimum analgesically effective dose of S-α-lipoic acid in the Randall-Selitto pain test is, for example, 1 mg/kg per os.

The minimum anti-inflammatorily effective dose of R-α-lipoic acid in the carragheen-induced oedema test is, for example, 1 mg/kg per os.

Similarly, both the R- and the S-form display cytoprotective activity in animal experiments with a dose of as little as 10 mg/kg per os.

In addition, R- and S-α-lipoic acid surprisingly possess a growth-inhibiting activity against retroviruses, in particular human immunodeficiency virus HIV (HIV-1, HIV-2) and are, therefore, also suitable for the treatment of disorders caused by viruses of this type.

They possess a good growth-inhibiting activity in HIV (Types 1 and 2) which may be demonstrated in vitro for example by means of the following virological and cell biological test procedures:

1. Plaque reduction test
2. CPE reduction test
3. Determination of reverse transcriptase in culture supernatant
4. Determination of p24 antigen in culture supernatant Thus, for example, a single dose of 0.035 mg/ml reduces the number of infectious viruses (for example HIV-1) in cell culture supernatant from 100% in the positive control to 0%. A virus-inhibiting activity can be demonstrated in this test procedure even in very small doses, for example 0.001 mg/ml.

The general dosage range for the activity (experiment as above) may for example be: 0.0035–0.091 mg/ml, in particular 0.035–0.070 mg/ml.

In the case of the in vitro experiments the active ingredient is used, for example in benzyl alcohol as solvent.

The following substrates may, for example, be used for the in vitro investigations of the replication behavior of retroviruses, in particular HIV:

1. Virus-containing RPMI 1640 medium, for example 1× liquid 041-01875 (synthetic culture medium from Gibco according to Moore, Gerner and Franklin, H. A. (1967), J.A.M.A. 199; 519) in a concentration of $2\times10^3$–$1\times10^4$ infectious units (PFU)/ml 2. The cell lines Jurkat Clone E6-1, Sup T1 and HeLa CT4.

The pharmaceutical formulations contain in general between 50 mg to 3 g as a single dose, preferably 100 mg to 1 g of R- or S-α-lipoic acid. The dose per kg of body weight should be between 3.5 and 200 mg, preferably between 7 and 100 mg, in particular between 35 and 70 mg/kg body weight.

The active ingredient should be released slowly from the formulations.

Administration may for example be in the form of tablets, capsules, pills, coated tablets, aerosols or suppositories, or in liquid form.

Liquid forms of application that may, for example, be considered are: alcoholic or aqueous solutions as well as suspensions and emulsions.

Preferred dosage forms are, for example, tablets containing between 100 mg and 2 g or solutions containing between 10 mg to 2 g/ml of liquid of active ingredient.

The single dose of active ingredient of may for example be:

a) in the oral medicinal form between 100 mg–3 g, preferably 200 mg–1 g.
b) in parenteral medicinal forms (for example intravenous, intramuscular) between 100 mg–12 g, preferably 200 mg–6 g.
c) in medicinal forms for inhalation (solutions or aerosols) between 100 mg–2 g, preferably 200 mg–1 g.
d) in medicinal forms for rectal or vaginal application between 100 mg–2 g, preferably 200 mg–1 g.

The doses according to a) to d) may for example be administered 1 to 6 times, preferably 1 to 4 times daily or, however, as a permanent infusion, for example with the aid of an infusoniate, i.e., with an infusion apparatus for accurate hourly dosage of an active substance in solution.

The daily dose of R- or S-α-lipoic acid in humans should for example be between 70–80 mg per kg weight; the single dose for example 16–20 mg per kg body weight, this dose appropriately being given 4 times daily: the pharmaceutical compositions therefore preferably contain 1–1.5 g of R- or S-α-lipoic acid in a pharmaceutical formulation, a dose of this type preferably being given 4 times each day.

The recommended treatment is, for example, 3 times daily, 1 to 4 tablets with a content of 50 mg to 2 g of active ingredient per tablet, or, for example, in intravenous injection 1 to 4 times daily, one ampoule/infusion bottle of 1 to 500 ml content with 200 mg to 6 g of active ingredient. In the case of oral administration the minimum daily dose is for example 300 mg; the maximum daily dose, given orally, should not exceed 12 g.

The pharmaceutical compositions may be used in human medicine alone or in a mixture with other pharmacologically active ingredients. The active ingredients R- or S-α-lipoic acid may also be combined with any other agent effective against retroviruses, in particular HIV, for example with didesoxyinosin, didesoxycytidine, in particular, however, with α-interferon and/or azidothymidine (AZT).

The dose amounts mentioned refer, in each case, to the free acids R- or S-α-lipoic acid. Should these be used in the form of their salts, the quoted dosages/dosage ranges should be increased in accordance with the higher molecular weight of the salts.

In the case of combinations with other antiretrovirally acting substances (component b) not only one, but also 2 and more (preferably 2) antiretrovirally active ingredients may be used as component b, the dosages cited therefor always referring to the sum of the antiretrovirally active ingredients present in each case.

The expression "dosage unit" always refers to a single dose which may also be administered several times daily.

If the dose is quoted in the form of enzyme units, this is the dose applicable for an entire day. A dose of this kind may be given once each day, but preferably is spread out over a whole day (for example in infusion form). The dose information in enzyme units applies in particular to α-interferon.

For the combination of R- or S-α-lipoic acid with the component b for example AZT, the two components may in each case be mixed for example in a ratio of 1 to 100 to 100 to 1 equimolar parts of active ingredient, in particular in a ratio of 1 to 10 to 10 to 1, preferably in a ratio of 1 to 3 to 3 to 1 parts.

In the case of a combination of R- or S-α-lipoic acid and α-interferon the two components may for example be present in the following ratio: 50 mg–6 g of R- or S-α-lipoic acid (component a) to $8\times10^6$ enzyme units to $1\times10^5$ enzyme units of α-interferon, in particular 0.5–3 g of component a to $1$–$4\times10^6$ enzyme units of α-interferon.

In the combination of R- or S-α-lipoic acid and other components in accordance with b), both components may be present as a mixture. In general, the components are, however, separated from one another in one pharmaceutical formulation, the pharmaceutical formulations known for this purpose being suitable for this purpose: for example one component as tablet or lacquered tablet, the other component as powder, both in one capsule and vice versa; one component in the form of pellets, the other as powder, coated tablet or talet and vice versa so that the two forms are present, for example, in one capsule; or in the form of multi-layer or laminated tablets. Reference is made in this context for example to the book "Arzneimittelstabilität" by Karl Thoma, Frankfurt 1978, for example page 207 et seq.

The combination of the invention may, however, also be present as a product in which in each case the two individual active ingredients may be present in formulations totally separated from one another, where component b in particular, but also both components (a and b) are contained in ampoules and/or infusion bottles, so that administration may occur separately or also at different times.

If totally different formulations of this type are present, these are adapted to each other and contain the appropriate active ingredients in the dosage unit in the same amounts and corresponding weight ratios in which they may be present in the combined mixture.

In the case of a product for separate use, it is also possible for both components of the combination to be administered at different times. In such cases it is for example possible to give R- or S-α-lipoic acid as a permanent infusion (dose for example 2–5 g per day) and the other component b to be given at the same time (dose for example 50–800 mg or 1–8×10⁶ enzyme units, preferably intramuscularly) or also as permanent infusion per day or R- or S-α-lipoic acid may, for example, be given 4 times daily (single dose for example 0.5–2 g) and the other component b at the same time (dose for example 50–200 mg or 0.5–3×10⁶ enzyme units). It is then possible for example for 1 to 3 further doses of component b (for example between 50–200 mg or 0.5–3× 10⁶ enzyme units) to follow after an interval of, in each case, 6 and/or 12 hours.

The formulations/products of the invention may preferably also contain additional vitamins, in particular vitamin $B_1$ and/or vitamin E.

For the treatment of disorders caused by retroviruses, in particular HIV viruses, appropriate pharmaceutical compositions should contain such an amount of R- or S-lipoic acid or this should be administered in such an amount, that single or repeated application achieves in the body a level of activity between 3.5 and 200 mg/kg, preferably 7 and 100 mg, in particular between 35 and 70 mg/kg body weight.

For the analgesic activity the general dose range of S-α-lipoic acid that may be considered is, for example:

1–100 mg/kg orally.

For the anti-inflammatory and cytoprotective activity the general dose range of R-α-lipoic acid that may be considered is, for example:

1–100 mg/kg orally.

Apart from its antinociceptive (analgesic) main activity, S-α-lipoic acid also possesses an anti-inflammatory and cytoprotective activity, however to a lesser extent.

In addition to the main anti-inflammatory and anti-arthritic activity, R-α-lipoic acid also has antinociceptive and cytoprotective activity, albeit to a lesser extent.

The optical isomers of α-lipoic acid display a good analgesic, anti-inflammatory, anti-arthrotic and cytoprotective activity in, for example, the following investigatory models:

$MgSO_4$ writhing test in the mouse according to GYIRES et al. (Arch. int. pharmacodyn. therap. 267, 131–140 (1984))

Adjuvans arthritis in the rat according to NEWBOULD (Brit. J. Pharmacol. 21, 127–136 (1963))

TPA- or arachidonic acid-induced mouse ear oedema according to YOUNG et al. (J. Invest. Dermatol. 80, 48–52 (1983))

Na-mono-iodazetate-induced arthrosis in rats or chickens according to KALBHEN in: Arthrosis deformans, EularVerlag, Basel/Switzerland, 1982

TPA-induced arthrosis in rats according to WEISCHER (Agents and Actions 23, ½ (1988))

Intestinal ulcerations in rats according to DEL SOLDATO (Agents and Actions 16, 393–396 (1985))

Colitis-model in the rat according to WEISCHER at al (Agents and Actions, vol. 26, ½, page 222 to 223, (1989))

Ethanol-ulcer model in the rat (determination for example of a cytoprotective activity).

The optical isomers of α-lipoic acid inhibit for example acute inflammation as well as inflammatory pain and they possess a specific cytoprotective activity.

Indications that may for example be considered are:

Inflammatory, degenerative articular and extra-articular rheumatic disorders, non-rheumatic states of inflammation and swelling, Arthrosis deformans, chondropathies, periarthritis, inflammatory and non-inflammatory skin disorders such as for example neurodermitis and psoriasis, inflammatory and non-inflammatory disorders of the gastrointestinal tract, such as for example gastritis, Ulcus ventriculi, ileitis, duodenitis, jejunitis, colitis, polyneuropathy of diabetogenic, alcoholic, hepatic and uraemic origin, degeneration of the liver parenchyma, hepatitis, fatty liver and fatty cirrhosis as well as chronic liver disorders, inflammatory respiratory tract disorders, such as bronchial asthma, sarcoidosis, ARDS (acute respiratory distress syndrome).

The daily doses of the dosage forms of the invention for analgesic or cytoprotective or anti-inflammatory activity are, for example, 0.1 to 600 mg, preferably 15 to 400 mg and in particular 50 to 200 mg of R-α-lipoic acid or S-α-lipoic acid.

In accordance with the invention the optical isomers of α-lipoic acid (R- or S-form in each case) are given in a daily dose of 10–600 mg, for example of 25 to 400 mg or 10 to 200 mg. The maximum daily dose for the cytoprotective activity and for the treatment of pain and inflammation should not exceed 600 mg. The daily doses may be given in the form of a single administration of the total amount or in the form of 1 to 6, in particular 1–4, partial doses per day. In general an administration of 1–4 times, in particular 1–3 times daily is preferred.

For example the preferred daily dose of both R-α-lipoic acid and S-α-lipoic acid is preferably 80 mg for the parenteral form of application and 200 mg for the oral form. In particular the daily dose for the parenteral form of application is 50 mg and 150 mg for the oral form.

The pharmaceutical compositions are preferably administered orally.

R-α-lipoic acid and S-α-lipoic acid may in particular also be applied in the form of a solution, for example perorally, topically, parenterally (intravenously, intraarticularly, intramuscularly, subcutaneously), as an inhalation, rectally, transdermally or vaginally.

Pharmaceutical compositions containing R-α-lipoic acid or S-α-lipoic acid as active ingredient may for example be formulated in the form of tablets, capsules, pills or coated tablets, granulates, pellets, plasters, solutions or emulsions, the active ingredient in each case optionally being combined with appropriate auxiliary and carrier substances. In the case of solutions, these contain for example 0.5 to 20% by weight, preferably 1 to 10% by weight of one of the optical isomers of α-lipoic acid (in each case either the R-form or S-form).

The dosage unit of the pharmaceutical composition with the optical isomers of α-lipoic acid or a therapeutically useful salt thereof (in each case either the R-form or the S-form) may, for example, contain:

a.) in the case of oral medicinal forms:

10 to 600 mg, preferably 20 to 400 mg, in particular 50 to 200 mg of the optical isomers of α-lipoic acid. The doses may for example be given 1 to 6 times, preferably 1 to 4 times, in particular 1 to 3 times daily. In each case, however, a total dosage of 600 mg per day should not be exceeded for the cytoprotective activity and for the treatment of pain and inflammation. The same also applies to the following medicinal forms listed under b) to e).

b.) in the case of parenteral medicinal forms (for example intravenous, intramuscular or intra-articular):

10 to 300 mg, preferably 15 to 200 mg, in particular 20 to 100 mg of the optical isomers of α-lipoic acid. The doses may, for example, be given 1 to 6 times, preferably 1 to 4 times, in particular 1 to 3 times daily.

c.) in the case of medicinal forms for application to the skin and mucous membranes (for example as solutions, lotions, emulsions, ointments, plasters and the like):

10 to 500 mg of R-α-lipoic acid or S-α-lipoic acid, preferably 40 to 250 mg, in particular 50 to 200 mg. These doses may for example be administered 1 to 6 times, preferably 1 to 4 times, in particular 1 to 3 times daily.

d.) In the case of medicinal forms for inhalation (solutions or aerosols):

0.1 to 300 mg, preferably 0.25 to 150 mg, in particular 0.5 to 80 mg of R-α-lipoic acid or S-α-lipoic acid. These doses may, for example, be administered 1 to 6 times, preferably 1 to 4 times, in particular 1 to 3 times daily.

Should lotions be used, the optical isomers of α-lipoic acid are preferably used in the form of a salt.

It is of course also possible to prepare pharmaceutical formulations which contain 2 to, for example, 6 times the above mentioned dosage units. In particular the tablets or capsules contain 20 to 500 mg, pellets, powders or granulates 20 to 400 mg, suppositories 20 to 300 mg of R-α-lipoic acid or S-α-lipoic acid.

To combat retroviruses (for example AIDS) the daily dose is for example 4–6 g. Corresponding pharmaceutical compositions therefore preferably contain R-α-lipoic acid or S-α-lipoic acid in the single dose (dose unit) for example in an amount of 600 mg to 1.5 g.

The above mentioned dosages always relate to the free optical isomers of α-lipoic acid. Should the optical isomers of α-lipoic acid be used in the form of a salt, the dosages/dosage ranges should be correspondingly increased due to the higher molecular weight.

The acute toxicity of R-α-lipoic acid and S-α-lipoic acid in the mouse (expressed as the LD50 mg/kg; method of LITCHFIELD and WILCOXON, J. Pharmacol. Exp Ther. 95, 99 (1949)), is for example in excess of 100 mg/kg in the case of oral administration.

In the event of the optical isomers of α-lipoic acid being used in animals, the following indications may be considered in particular: hepatoses, Arthrosis deformans, arthritis and dermatitis.

The following dosages may for example be considered for the treatment of animals (both R-form and S-form):

For the treatment of cats, the oral single dose generally lies between about 2 mg/kg and 50 mg/kg body weight, the parenteral dose about between 0.5 and 40 mg/kg body weight.

For the treatment of arthroses in horses and cattle, the oral single dose generally lies between about 2 mg/kg and 100 mg/kg body weight, the parenteral dose about between 0.5 and 50 mg/kg body weight.

The individual optical isomers of α-lipoic acid are suitable for the preparation of pharmaceutical compositions and formulations. The pharmaceutical compositions and/or pharmaceutical compositions contain the optical isomers of α-lipoic acid as active ingredient, optionally in a mixture with other pharmacologically and/or pharmaceutically active ingredients. The preparation of the pharmaceutical compositions is effected in known manner, it being possible to use known and conventional pharmaceutical auxiliary substances as well as other conventional carrier and diluting agents. Carrier and auxiliary substances of this type which may for example be considered are those recommended or quoted in the following literature references as auxiliary substances for pharmacy, cosmetics and associated fields: "Ullmanns Enzyklopädie der technischen Chemie, Volume 4 (1953), page 1 to 39; Journal of Pharmaceutical Sciences", Volume 52 (1963), page 918 et seq., H. v. Czetsch-Lindenwald, "Hilfsstoffe für Pharmazie und angrenzende Gebiete"; Pharm. Ind. Issue 2 (1961), page 72 et seq.; Dr. H. P. Fiedler, "Lexikon der Hilfsstoffe für Pharmazie, Kosmetik und angrenzende Gebiete", Cantor KG, Aulendorf in Württemberg (1989).

The pharmaceutical and galenic treatment of the R- or S-α-lipoic acid is carried out using conventional standard methods. For example R- or S-α-lipoic acid and auxiliary or carrier substances may be well mixed by stirring or homogenization (for example using conventional mixing apparatus), working generally being at temperatures between 20° and 50° C., preferably 20° to 40° C., in particular at room temperature. For further particulars reference is made to the following standard work: Sucker, Fuchs, Speiser, "Pharmazeutische Technologie", Thieme-Verlag Stuttgart, 1978.

Application of the R- or S-α-lipoic acid or of the pharmaceutical compositions may be to the skin or mucous membrane or to the inside of the body, for example oral, enteral, pulmonal, rectal, nasal, vaginal, lingual, intravenous, intra-arterial, intracardial, intramuscular, intraperitoneal, intracutaneous, subcutaneous administration.

The parenteral formulation forms are in particular sterile or sterilized products.

If the R- or S-α-lipoic acid are used in the form of their salts, the salt formers may also be used in excess, i.e. in an amount greater than equimolar.

Examples of carrier and auxiliary substances are gelatin, natural sugars such as raw sugar or lactose, lecithin, pectin, starches (for example corn starch or amylose), cyclodextrins and cyclodextrin derivatives, dextran, polyvinylpyrrolidone, polyvinyl acetate, gum arabic, alginic acid, tylose, talcum, lycopodium, silicic acid (for example colloidal), cellulose, cellulose derivatives (for example cellulose ethers, in which the cellulose-hydroxy groups are partially etherified with lower saturated aliphatic alcohols and/or lower saturated aliphatic oxyalcohols, for example methyloxypropyl cellulose, methyl cellulose, hydroxypropylmethyl cellulose, hydroxypropylmethyl cellulosephthalate); fatty acids as well as magnesium, calcium or aluminium salts of fatty acids with 12 to 22 carbon atoms, in particular saturated (for example stearates), emulsifiers, oils and fats, in particular vegetable (for example peanut oil, castor oil, olive oil, sesame oil, cottonseed oil, corn oil, wheat germ oil, sunflower seed oil, cod liver oil, in each case also hydrated); glycerol esters and polyglycerol esters of saturated fatty acids $C_{12}H_{24}O_2$ to $C_{18}H_{36}O_2$ and their mixtures, the glycerol hydroxy groups being totally or only partially esterified (for example mono, di and triglycerides); pharmaceutically acceptable single or multivalent alcohols and polyglycols as well as polyethylene glycols (molecular weight range for example 300 to 1500) as well as derivatives thereof, polyethylene oxide, esters of aliphatically saturated or unsaturated fatty acids (2 to 22 carbon atoms, in particular 10–18 carbon atoms) with monovalent aliphatic alcohols (1 to 20 carbon atoms) or multivalent alcohols such as glycols, glycerol, diethylene glycol, pentaerythritol, sorbitol, mannitol and the like, which may optionally also be etherified, esters of citric acid with primary alcohols, acetic acid, urea, benzylbenzoate, dioxolanes, glycerol formals, tetrahydrofurfuryl alcohol, polyglycol ether with $C_1$–$C_{12}$ alcohols, dimethylacetamide, lactamides, lactates, ethylcarbonates, silicons (in particular medium-viscous polydimethylsiloxanes), calcium carbonate, sodium carbonate, calcium phosphate, sodium phosphate, magnesium carbonate and the like.

Other auxiliary substances that may be considered are those which promote disintegration (so-called disintegrants), such as: cross-linked polyvinylpyrrolidone, sodium carboxy methyl starch, sodium carboxy methyl cellulose or microcrystalline cellulose. It is also possible to use known coating substances. These may, for example, be: polymerizates as well as copolymerizates of acrylic acid and/or methacrylic acid and/or their esters; copolymerizates of acrylic and methacrylic acid esters with a low ammonium group content (for example Eudragit$^R$ RS), copolymerizates of acrylic and methacrylic acid esters and trimethylammonium methacrylate (for example Eudragit$^R$ RL); polyvinyl acetate; fats, oils, waxes, fatty alcohols; hydroxypropylmethylcellulose phthalate or -acetate succinate; cellulose acetate phthalate, starch acetate phthalate as well as polyvinyl-acetate phthalate; carboxymethyl cellulose; methylcellulose phthalate, methylcellulose succinate, -phthalate succinate as well as methylcellulose-phthalic acid half ester; zein; ethyl cellulose as well as ethylcellulose succinate; shellac, gluten; ethylcarboxyethyl cellulose; ethacrylate-maleic acid anhydride copolymer; maleic acid anhydride-vinylmethyl ether copolymer; styrol-maleic acid copolymerizates; 2-ethyl-hexyl-acrylate maleic acid anhydride; crotonic acid-vinylacetate copolymer; glutaminic acid/glutaminic acid ester copolymer; carboxymethylethylcellulose-glycerol monooctanoate; celluloseacetate succinate; polyarginin.

Plasticizing agents that may be used as coating substances are:

citric and tartaric acid esters (acetyltriethyl citrate, acetyltributyl-, tributyl-, triethyl citrate); glycerol and glycerol esters (glycerol diacetate, -triacetate, acetylated monoglycerides, castor oil); phthalic acid esters (dibutyl-, diamyl-, diethyl-, dimethyl-, dipropyl phthalate), di-(2-methoxy- or 2-ethoxy ethyl)-phthalate, ethylphthalyl glycolate, butylphthalyl ethyl glycolate and butyl glycolate; alcohols (propylene glycol, polyethylene glycol of various chain lengths), adipates (diethyl-adipate, di-(2-methoxy- or 2-ethoxyethyl)-adipate); benzophenone; diethyl- and dibutylsebacate, dibutyl succinate, dibutyl tartrate; diethylene glycol diproprionate; ethylene glycoldiacetate, -dibutyrate, -dipropionate; tributyl phosphate, tributyrin; polyethylene glycol sorbitan monooleate (polysorbates such as Polysorbat 80); sorbitan monooleate.

To prepare solutions or suspensions it is for example possible to use water or physiologically acceptable organic solvents such as for example alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, cattle hoof oil), paraffins, dimethyl sulfoxide, triglycerides and the like.

For injectable solutions or suspensions it is for example possible to use non-toxic parenterally acceptable diluents or solvents, such as for example: water, 1,3-butane diol, ethanol, 1,2-propylene glycol, polyglycols in mixture with water, glycerol, Ringer's solution, isotonic cooking salt solution or also hardened oils including synthetic mono- or diglycerides or fatty acids such as oleic acid.

In preparing the formulations it is possible to use known and conventional solubilizers or emulsifiers. Solubilizers and emulsifiers which may for example be used are: polyvinylpyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolisated oleotriglycerides, polyethylene oxide condensation products of fatty alcohols, alkylphenols or fatty acids or also 1-methyl-3-(2-hydroxyethyl)imidazolidone-(2). Polyoxyethylated here means that the substances in question contain polyoxyethylene chains, the degree of polymerization of which generally lies between 2 and 40 and in particular between 10 and 20. Polyoxyethylated substances of this kind may for example be obtained by reacting hydroxyl group-containing compounds (for example mono- or diglycerides or unsaturated compounds such as those containing oleic acid radicals) with ethylene oxide (for example 40 mol of ethylene oxide per 1 Mol glyceride).

Examples of oleotriglycerides are olive oil, peanut oil, castor oil, sesame oil, cottonseed oil, corn oil.

See also Dr. H. P. Fiedler "Lexikon der Hilfsstoffe für Pharmazie, Kosmetik und angrenzende Gebiete" 1971, p. 191–195.

In addition, it is also possible to add preservatives, stabilizers, buffer substances, flavor correcting agents, sweeteners, colorants, antioxidants and complex formers and the like.

Complex formers that may for example be considered are: chelate formers such as ethylene diamine tetraacetic acid, nitrilotriacetic acid, diethylenetriamine pentaacetic acid and salts thereof.

Complex formers that may be considered include those which enclose the R- or S-α-lipoic acid acid in a hollow space. Examples hereof are urea, thiourea, cyclodextrins, amylose. The active molecule substance may optionally be stabilized With physiologically acceptable bases or buffers to a pH range of ca. 6 to 9. Preference is in general given to as neutral or weakly basic a pH value as possible (up to pH 8).

Antioxidants that may for example be used are sodium sulphite, sodium hydrogen sulphite, sodium metabisulphite, ascorbic acid, ascorbyl palmitate, -myristate, -stearate, gallic acid, gallic acid alkyl ester, butylhydroxyanisol, nordihydroguaiacic acid, tocopherols as well as synergists (substances that bind heavy metals through complex formation, for example lecithin, ascorbic acid, phosphoric acid ethylene diamine tetraacetic acid, citrates, tartrates). The addition of the synergists substantially enhances the antioxygenic activity of the antioxidants.

Preservatives that may for example be considered are sorbic acid, p-hydroxybenzoic acid esters (for example lower alkyl esters), benzoic acid, sodium benzoate, trichloroisobutyl alcohol, phenol, creosol, benzethonium chloride, chlorhexidine and formalin derivatives.

DETAILED DESCRIPTION OF PREFERRED EMBODIMENTS

The following is a brief description of the test methods used in the experiments described below:

Randall-Selitto test (inflammatory pain in the rat)

By analogy with the method according to RANDALL and SELITTO (L. O. Randall and J. Selitto, Arch. int. Pharmacodyn. Vol. 111, pages 409–418 (1957)), rats receive subplantar injections of 0.1 ml of a 20% (in demineralized water) brewer's yeast suspension into the right back paw. 2 ½ hours thereafter the test substances are administered and 30 minutes thereafter the pain threshold (in grams) is measured as pain in the inflamed paw using a commercially available algesia meter. The criterion is the defense reaction shown by the animals in pulling the paw away and/or freeing themselves from the research worker's grip. The activity of the substance is measured in the form of the increase in the pain threshold as compared to an untreated control group. The course of the experiment differs from that in the original method in that the substances are only given 2-½ hours after provocation of the edema and not simultaneously therewith. In so doing the intention is to prevent the development of the edema being inhibited by a possible anti-inflammatory activity and masking or feigning analgesia.

The $ED_{50}$ is determined using the linear regression method. The $ED_{50}$ here is the dose in mg/kg at which mathematically there is a 50% analgesic activity.

Acetic acid test (writhing test) in the mouse
Method:

In the acetic acid test after KOSTER et al. (Fed. Proc., Vol. 18, page 412 (1959)) the pain stimulus is triggered by an intraperitoneal injection of 1% acetic acid. The pain reaction is expressed in the form of the characteristic stretching of the animals ("writhing syndrome") which continues at irregular time intervals for some time after injection of the acetic acid. The dose-dependent inhibition of the frequency of the stretching movement as compared to an untreated control group is expressed in percent as analgesic activity. Evaluation is by determination of the $ED_{50}$ (Method of linear regression). The $ED_{50}$ is the dose in mg/kg at which there is a 50% inhibition of the "writhing syndrome".

The acetic acid test is characterized in that it not only demonstrates the activity of strong, centrally acting analgesics, but also that of predominantly peripherally active analgesic-antipyretic agents and anti-inflammatory pharmaceuticals, such as phenylbutazone, indomethacin and the like. The activity in the experimental design suggests a peripheral component of the analgesia.

Caragheen-induced edema test for anti-inflammatory activity:

The investigation is conducted in carragheen-induced edema of the rat paw after the method of MOERSDORF and coworkers (Arch. int. Pharmacodyn. 192, 111-127 (1971)). The anti-inflammatory activity is, for example, given as inhibition of edema in percent as compared to the untreated control group. Application is oral or intraperitoneal in all experiments. The substance is administered orally or intraperitoneally 1 hour after triggering the inflammation. The $ED_{50}$ is the dose in mg/kg at which there is 50% inhibition of the paw oedema.

EXAMPLE 1

Tablets Containing 50 mg of S- or R-α-Lipoic Acid 250 g of S-α-lipoic acid are evenly ground with 750 g of microcrystalline cellulose. After sieving the mixture, 250 g of starch (starch 1500/Colorcon), 732.5 g of lactose, 15 g of magnesium stearate and 2.5 g of highly disperse silicon dioxide are mixed therein and the mixture is pressed into tablets weighing 400.0 mg.

Each tablet contains 50 mg of S-α-lipoic acid.

In similar manner it is possible to prepare tablets containing 50 mg of R-α-lipoic acid when the 250 g of lipoic acid is replaced by the same amount of R-α-lipoic acid.

The tablets may optionally be provided with a gastric juice soluble or gastric juice permeable film coating using conventional methods.

EXAMPLE 2

Ampoules Containing 50 mg of S- or R-α-Lipoic Acid as Tromethamine Salt in 2 ml 250 g of S-α-lipoic acid are dissolved with stirring together with 352.3 g of tromethamine (2-amino-2-(hydroxymethyl)-1,3-propane diol) in a mixture of 9 liters of sterile deionized water and 200 g of 1,2-propylene glycol. The solution is diluted to 10 liters with sterile deionized water and then filtered through a membrane filter of pore size 0.2 μm using a glass fiber pre-filter. The filtrate is filled under aseptic conditions in 2 ml batches into sterilized 2 ml ampoules.

One ampoule contains 50 mg of S-α-lipoic acid as tromethamine salt in 2 ml of injection solution.

The same procedure may be used to prepare ampoules with R-α-lipoic acid by using the same amount of R-α-lipoic acid in place of 250 g of S-α-lipoic acid.

What is claimed is:

1. A pharmaceutical composition consisting essentially of a pharmaceutically effective carrier and, as active ingredient, an effective amount of R-α-lipoic acid or a pharmaceutically acceptable salt thereof.

2. A pharmaceutical composition as set forth in claim 1 which is a solution containing R-α-lipoic acid as active ingredient and also a member of the group consisting of stabilizers and solubilizers.

3. A pharmaceutical composition as set forth in claim 2 in which the stabilizer or solubilizer is selected from the group consisting of aliphatic $C_2$-$C_4$-alcohol which contain one, two or three hydroxyl groups, polyethylene glycol of molecular weights between 200 and 600; conventional physiologically acceptable organic amide, natural - aminoacid, aliphatic amine, hydroxyethyl theophylline, tromethamine, diethyleneglycol monomethylether.

4. A pharmaceutical dosage unit containing the pharmaceutical composition set forth in claim 1 in an amount such that the R-α-lipoic acid is in each case present in an amount of 0.1 mg to 6 g.

5. A pharmaceutical dosage unit containing the pharmaceutical composition set forth in claim 1 in an amount such that the R-α-lipoic acid is in each case present in an amount of 0.1 to 600 mg.

6. A tablet containing the pharmaceutical composition set forth in claim 1 in an amount such that the R-α-lipoic acid is in each case present in an amount of between 100 mg and 2 g.

7. A dosage unit of a solution suitable for parental administration containing the pharmaceutical composition set forth in claim 1 in an amount such that the R-α-lipoic acid is in each case present in an amount of 100 mg–12 g.

8. A dosage unit of a solution suitable for parental administration containing the pharmaceutical composition set forth in claim 1 in an amount such that the R-α-lipoic acid is in each case present in an amount of 200 mg–6 g.

9. A method of combatting inflammatory, degenerative articular and extra-articular rheumatic disorders, non-rheumatic states of inflammation and swelling, Arthrosis deformans, chondropathies, periarthritis, neurodermitis and psoriasis, gastritis, Ulcus ventriculi, ileitis, duodenitis, jejunitis, colitis, polyneuropathy of diabetogenic, alcoholic, hepatic and uraemic origin, degeneration of the liver parenchyma, hepatitis, fatty liver and fatty cirrhosis as well as chronic liver disorders, bronchial asthma, sarcoidosis, ARDS (acute respiratory distress syndrome) which comprises administering an effective amount of the pharmaceutical composition of claim 1.

10. The pharmaceutical composition of claim 3 wherein said stabilizer is tromethamine.

* * * * *